United States Patent [19]

Massen et al.

[11] Patent Number: 5,386,292
[45] Date of Patent: Jan. 31, 1995

[54] OPTICAL MEASUREMENT OF TEETH

[75] Inventors: Robert Massen, Wangen/Öhningen; Joachim Gassler, Geisingen; Christian Konz, Radolfzell; Harald Richter, Constance, all of Germany

[73] Assignee: Kaltenbach & Voight GmbH & Co., Biberach, Germany

[21] Appl. No.: 53,712

[22] Filed: Apr. 27, 1993

[30] Foreign Application Priority Data

May 5, 1992 [DE] Germany .................... 4214876

[51] Int. Cl.⁶ .................... G01B 11/03; G01B 11/24
[52] U.S. Cl. ........................ 356/376; 250/561
[58] Field of Search ............. 356/375, 376; 250/560, 250/561

[56] References Cited

U.S. PATENT DOCUMENTS 4,935,635  6/1990  O'Harra .................... 356/376

FOREIGN PATENT DOCUMENTS 0234422  9/1987  European Pat. Off. .
0299490  1/1989  European Pat. Off. .

Primary Examiner—F. L. Evans
Attorney, Agent, or Firm—Scully, Scott, Murphy & Presser

[57] ABSTRACT

3D tooth measurement by means of an optical probe wherein a prior matting treatment of the tooth to be measured can be dispensed with. The consequential reflection-dependent measuring errors are compensated by an error correction method.

12 Claims, 3 Drawing Sheets

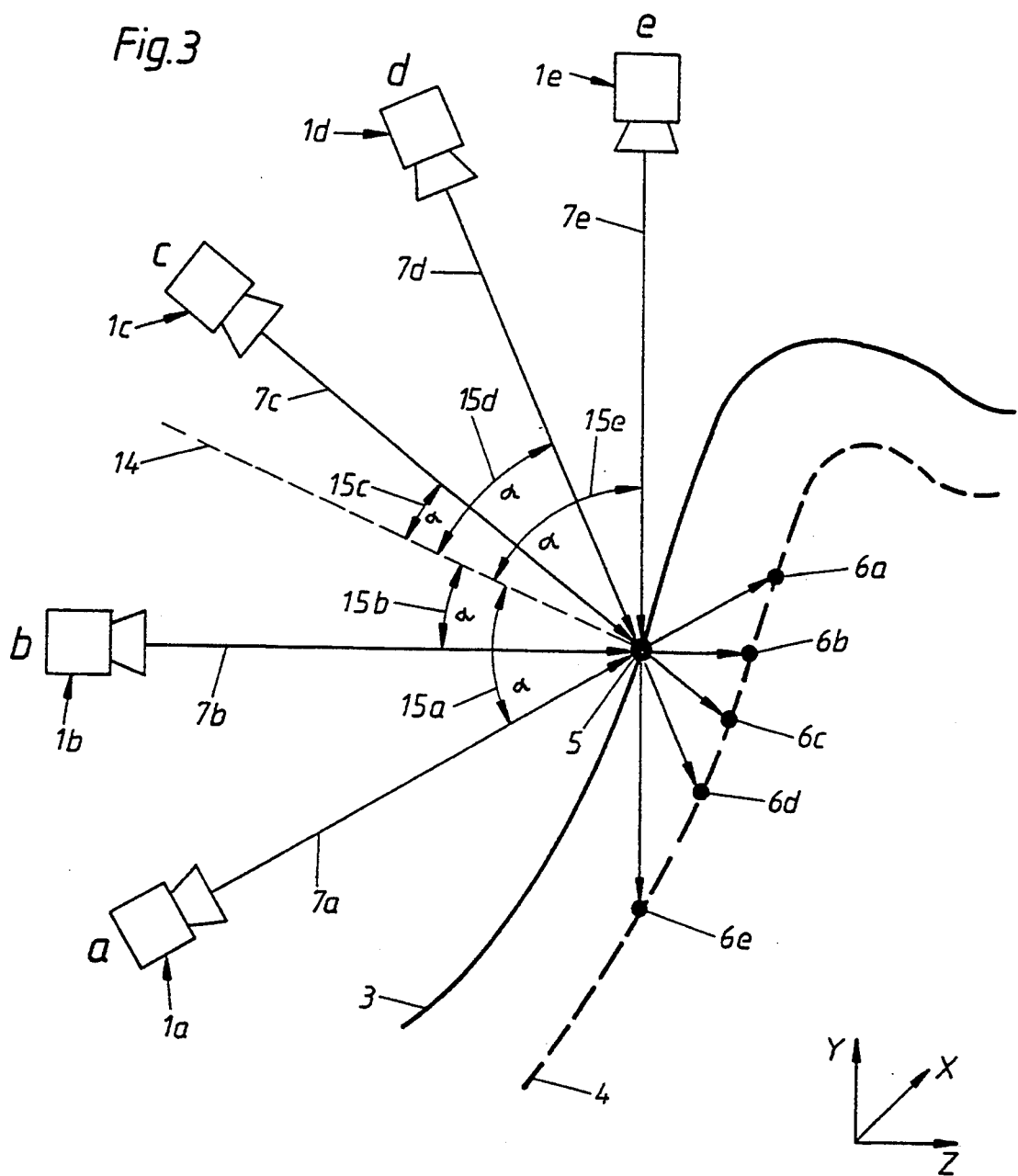

OPTICAL MEASUREMENT OF TEETH

TECHNICAL FIELD OF THE INVENTION

The present invention relates to a method for optically measuring teeth, in which an initial surface treatment of the teeth to improve the reflection qualities can be dispensed with because the measured tooth coordinates can be corrected by means of correction values.

BACKGROUND OF THE INVENTION

Methods for optical measurement of teeth and the subsequent automatic manufacture of dentures are generally known, e.g. from EP 0299490. Here the tooth is measured by means of an optical measuring method according to the Moirée, phase-shift or triangulation technique. In all these measuring methods it is assumed that the surface of the tooth reflects optimally, e.g. perfect diffusion (Lambert's reflection). Since this is not the case as a general rule, these methods regularly supply inaccurate data which result in the automatically manufactured dentures having bad fitting accuracy.

FIGS. 1a to 1c clearly show the different reflection qualities of a tooth and their effects with regard to determining the tooth coordinates. In FIG. 1a the surface of the tooth enamel is partly transparent (translucence) which results in the optical rays penetrating it. Thereby, in the measurement process, systematically too-small tooth dimensions are obtained. This effect depends on the direction of the ray striking the tooth surface relative to the tooth surface.

FIG. 1b shows a further optical difficulty when measuring the tooth, which is that the shiny tooth surface reflects partly directionally. This results in a displacement of the projected pattern and therefore also to inaccurate measurement of the tooth coordinates.

FIG. 1c, on the other hand, shows a perfectly-diffuse reflection as is required in the methods of the state of the art mentioned above.

These non-optimal reflection qualities of the tooth have been determined in the course of time, and thereby eliminated by coating the tooth to be measured by means of matting substances such as, e.g. chalk solutions, titanium dioxide powder or the like. Thus, for example, with the known CEREC method a measurement powder is sprayed onto the tooth to make its surface opaque and reflection-free. Furthermore disclosed in the state of the art (EP-A-0234422) is a method for improving the reflecting power. Therein the tooth is coated with a suspension that contains white pigments in an aqueous alcoholic solution in order in this way to improve the reflecting qualities of the tooth.

A disadvantage is that this pre-treatment increases the treatment time noticeably and is extremely unpleasant for the patient. Furthermore this method requires as thin and as uniform a layer thickness as is possible. Irregularities in the layer thickness are difficult to control and therefore lead to inaccuracies in the measurement data.

OBJECT OF THE INVENTION

It is an object of the invention to disclose a measuring method which avoids the disadvantages mentioned above.

SUMMARY OF THE INVENTION

According to a first aspect of the present invention, there is provided a method of optical measurement of teeth, comprising a first step of optically measuring a surface of a tooth to determine measured coordinate values of a plurality of measured points on said tooth surface, and a second step of performing error correction upon at least some of said measured co-ordinate values to determine corrected co-ordinate values of said tooth surface.

According to a second aspect of the present invention, there is provided a method for determining correction values for error correction of optically measured coordinate values of the surface of a tooth, wherein:

the exact coordinate values of any desired point on the tooth surface are determined and stored as reference coordinate values;

the desired point is furthermore measured optically from different projection/pick-up positions of a measuring apparatus in such a way as to be subject to measuring errors caused by reflection; and in that the differences between the reference coordinate values and the measured coordinate values are calculated for each projection/pick-up position and stored as said correction values together with a corresponding projection/pick-up position value.

BRIEF DESCRIPTION OF THE DRAWINGS

The method according to the invention will be explained by way of example with reference to the following drawings, in which:

FIG. 3 shows the determination of the error correction values.

DETAILED DESCRIPTION

Figure 1A:
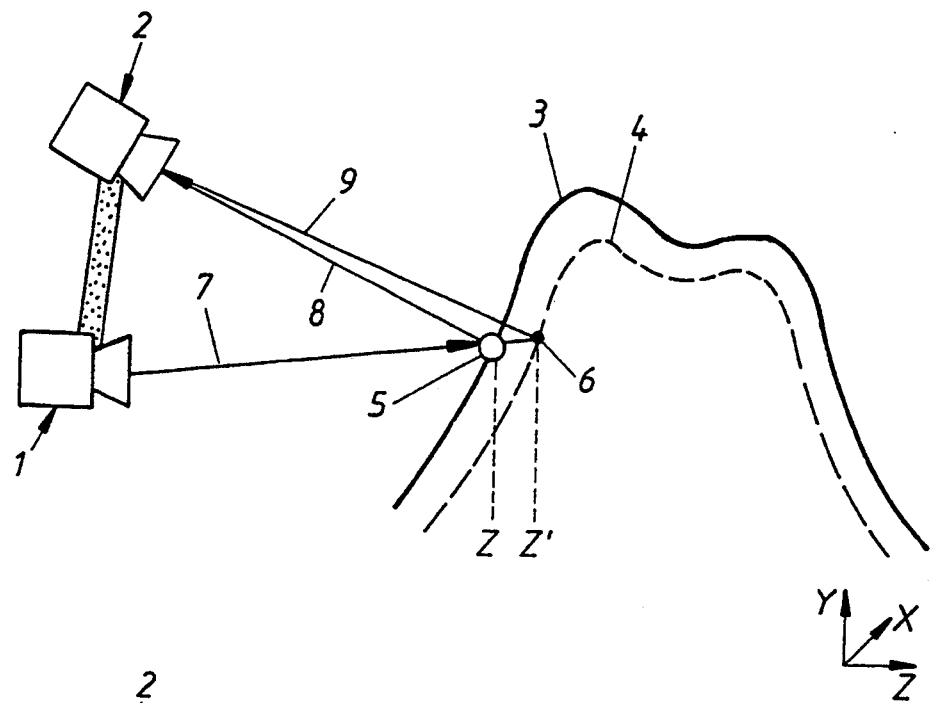
FIGS. 1a to c show, by way of example, the paths of rays with a tooth having a a) translucent, b) irregularly reflecting and c) matt, diffusely reflecting surface.
Figure 1B:
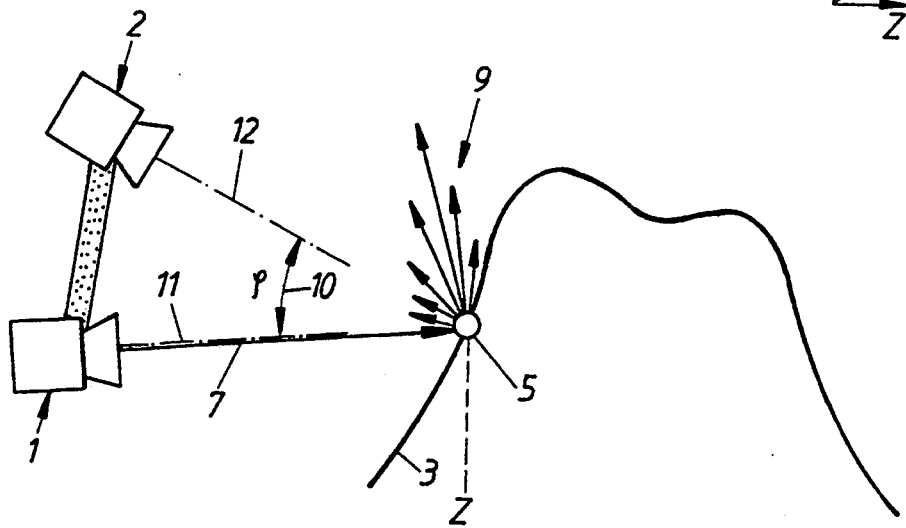
Figure 1C:
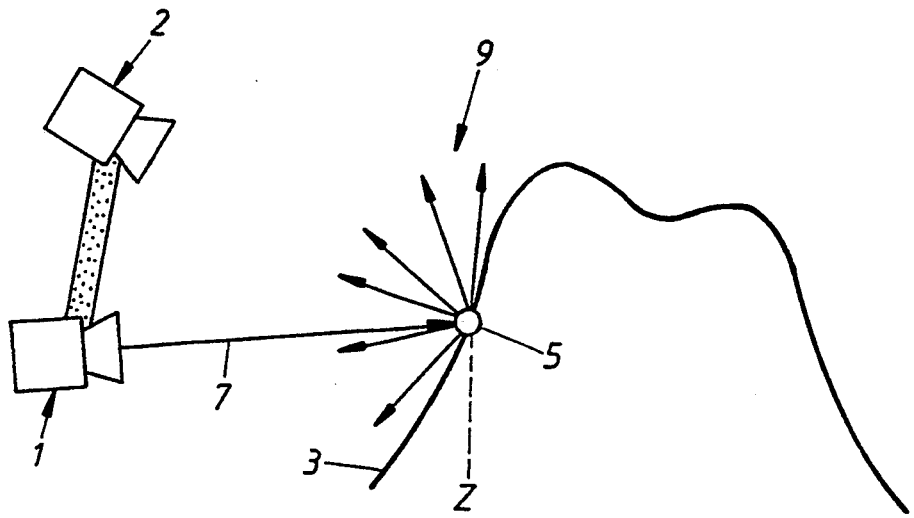
Figure 2:
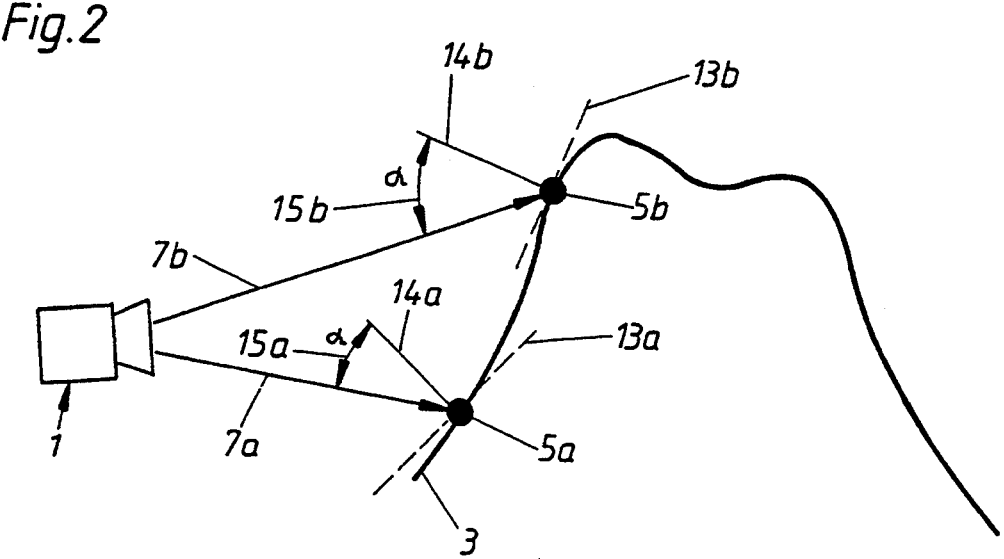
FIG. 2 shows, by way of example, the construction of a surface vector and the determination of the angle $\alpha$.

As is indicated only in outline in FIGS. 1 to 3, the optical measurement device comprises a light pattern projector and an image sensor which are arranged at a parallax angle $\phi$ which, as a rule, is constant. It is known from the patent application DE-A-38 29 925 by the present to use for the light pattern projector a matrix light modulator with freely programmable transmission values for each image point, and to use as a light pattern strips having a sine-shaped amplitude modulation. Usually a CCD matrix image sensor is used as an image sensor, if necessary with a coherent light guide mounted thereon. For the purpose of further explanation a single point of the tooth surface is considered that has the spatial coordinates (XYZ) and is illuminated by the projector and detected by the sensor. For simplicity this view is based on a sectional image and only the coordinate Z is discussed. It is known to the person skilled in computer graphics how this 2 D explanation can be applied to the in reality 3-dimensional problem.

FIG. 1a shows schematically the effects of an optical characteristic of the tooth that is based on the translucence of the tooth enamel. With a translucent tooth surface 3, not all the light striking the tooth surface 3 will be reflected but a certain proportion penetrates into the tooth enamel and is there dispersed mainly to a further interior boundary or surface 4. This dispersion occurs within the material in a spatial angle of $4\pi$. The fractions of light dispersed into the direction of observation lead to an asymmetrical distortion of the point image on the surface which, when determining the centre of gravity, causes an offset centre of gravity.

In FIG. 1a this offset centre of gravity is indicated by an inner point 6 that is calculated by means of the centre of gravity ray 9 in place of the ray 8 detected with regular reflection (Fresnel reflection). A regular reflection only occurs at the boundary area between two media with different refractive indices. This is the case at the surface of the tooth, at fine structures (particles) within the tooth (little enamel rods) or possibly at the boundary area to the dentine if the two fractions are different although this is unlikely.

FIG. 1b shows the case of a non-ideal diffuse, partly directional reflection. Here the centre of gravity of the reflected intensity of the rays 9 is displaced towards its angle of reflection which would arise with a completely reflecting reflection. The light pattern detected by the image sensor 2 would thereby also be displaced, so that in this case too, an incorrect coordinate value of the considered point 5 on the tooth surface 3 would be calculated.

For clarity in FIG. 1b only the parallax angle 10 formed by the optical axes 11 and 12 of the light pattern projector 1 and the image sensor 2 is given. Such an arrangement of the image projection/pick-up system for carrying out an optical measurement process with the Moirée-, phase-shift- and triangulation technique is indispensable.

In the two cases just considered the resulting measurement error depends systematically on the orientation of the incident measuring rays 7 relative to the tooth surface 3. If, for example, the light pattern projector 1 shown in FIG. 1a were to be moved downwards so that the measuring ray 7 strikes the point 5 more obliquely, the point 6 thus wanders upwards onto the inner surface 4. A great change in the Y-coordinate value would accordingly be detectable.

Only with an ideal diffusely reflecting surface, as is shown in FIG. 1c, do no changes occur in the measured spatial coordinate values as a function of the orientation of the incident measuring rays.

According to the invention these non-optimal reflecting qualities of the tooth surface which lead to errors are now taken into consideration.

In a first method step the coordinate values describing the tooth contour 3 are calculated, wherein these coordinate values contain errors for the reasons mentioned above. These values are then stored in a memory.

In a subsequent step the surface vector for some of these coordinate values or for all of these coordinate values is determined and stored with regard to the corresponding coordinate value. This surface vector is used to determine the angle of incidence of the measuring rays on the tooth surface because, as already explained in the introduction, the measuring error depends on the orientation of the measuring ray.

With reference to FIG. 2, determination of the surface vectors will now be explained by way of example at two points 5a, 5b. From the first measuring step a rough contour of the tooth surface 3, containing errors, is known. By means of a known geometric method, an auxiliary plane 13a and 13b is placed through the points 5a and 5b respectively, which contains at least two further measured points lying in the near vicinity. A plane is, as known, sufficiently defined by three points.

A perpendicular 14a or 14b is then formed on each of these auxiliary planes that goes through the point 5a or 5b, respectively.

The perpendicular 14a, 14b designated as a surface vector and standing on its auxiliary plane 13a, 13b, is stored in a memory with a reference (association) to the respective point 5a, 5b.

Since, as already mentioned, the measuring error depends on the orientation of the measuring ray 7, an angle 15 may be given between the surface vector 14 and the measuring ray 7 in relation to a point 5, which is a measure of the size of the error.

For example, a correction value can be read from a stored table with reference to the angle $\alpha$, which is combined with the erroneous coordinate value by addition or multiplication and which results in an error-free coordinate value.

This error correction can be carried out for all roughly measured points, or only for selected points of the roughly measured tooth contour with the points lying therebetween being interpolated.

How such a dependency between the orientation of the measuring ray, i.e. of the angle $\alpha$, and a corresponding correction value is obtained, is described with reference to FIG. 3.

Any desired point 5 on the tooth surface 3 is measured exactly in a first step. By applying, for example, a small matting spot on this point the reflection quality of the tooth can be altered so that it becomes substantially optimal. At the same time the surface vector 14 for this point 5 is calculated and stored together with the tooth coordinate values.

In a next step the light pattern projector 1 is moved in succession into different positions relative to the point 5. Depending on the position of the projector 1 and a corresponding angle 15a to e, the result of the measurement does not give the coordinate values of the point 5 but those of the points 6a to e. With reference to the exactly measured coordinate values 5 and the error-containing points 6a to e, the correction values which are the difference between the error-containing false value and the exact coordinate value, can be calculated. This correction value is stored together with the corresponding angle in a memory. The correction value for the other angles can be interpolated by means of the known angles and the correction values.

The inventors have discovered in many series of tests that the optical properties of the tooth examined at any desired point 5 can be transferred to all other regions of the tooth.

It is therefore also possible to determine the correction values with reference to an easily accessible tooth of a patient or even to determine it outside the mouth of the patient empirically with reference to typical tooth materials.

It would of course also be possible to determine the correction values mathematically by specifying, for example, the layer thickness of the translucent layer without taking measurements of the tooth.

According to the invention image points having insufficient brightness and/or contrast of the projected light pattern are automatically cut out and marked in the image memory. The missing coordinate values of these image points are replaced by an interpolation of the coordinate values of the valid points surrounding it.

What is claimed is:

1. A method of optical measurement of teeth, comprising a first step of optically measuring a surface of a tooth to determine measured coordinate values of a plurality of measured points on said tooth surface, and a second step of performing error correction upon at least some of said measured co-ordinate values to determine corrected co-ordinate values of said tooth surface wherein a correction value used for the error correction in said second step is determined using a value which depends upon the position of the point to be corrected and the position of a projection system used in said first step.

2. A method according to claim 1, wherein said second step is performed for only some of said measured points, and wherein uncorrected points are interpolated with reference to the corrected points.

3. A method according to claim 1, wherein in said second step all the measured co-ordinate values are subjected to error correction.

4. A method according to claim 1, wherein the value depending on the position of the point to be corrected and the position of the projection system is in the form of an angle.

5. A method according to claim 4, wherein said angle is formed between a surface normal going through the measured point relative to the tooth surface and a measuring light ray incident on the measured point.

6. A method according to claim 5, wherein after the first step, the surface normal for each measured point is determined mathematically and stored.

7. A method for determining correction values for error correction of optically measured coordinate values of the surface of a tooth, wherein:

the exact coordinate values of any desired point on the tooth surface are determined and stored as reference coordinate values;

the desired point is furthermore measured optically from different projection/pick-up positions of a measuring apparatus in such a way as to be subject to measuring errors caused by reflection; and in that the differences between the reference coordinate values and the measured coordinate values are calculated for each projection/pick-up position and stored as said correction values together with a corresponding projection/pick-up position value.

8. A method according to claim 7, wherein each said projection/pick-up position value is given as an angle between a measuring ray incident on the desired point and a surface normal going through the desired point.

9. A method according to claim 7, wherein the reference coordinate values are determined by deliberate matting of at least a portion of said tooth surface and subsequent optical measurement of said portion.

10. A method according to claim 7, wherein further correction values are interpolated with reference to said calculated correction values.

11. A method according to claim 7, wherein said tooth is in the form of typical tooth material outside the mouth of a patient, so that the correction values are determined outside the mouth.

12. A method according to claim 7, said tooth is an easily accessible tooth within the mouth of a patient, so that the correction values are determined in the mouth.

* * * * *